US00PP09450P

United States Patent [19]

Lamb et al.

[11] Patent Number: Plant 9,450

[45] Date of Patent: Feb. 6, 1996

[54] ANTHURIUM PLANT NAMED 'PASSION'

[75] Inventors: Ann E. Lamb, Sebring; Robert D. Hartman, Lake Placid, both of Fla.

[73] Assignee: Twyford International, Inc., Santa Paula, Calif.

[21] Appl. No.: 382,790

[22] Filed: Feb. 2, 1995

[51] Int. Cl.[6] ..... A01H 5/00

[52] U.S. Cl. ..... Plt./88.1

[58] Field of Search ..... Plt./88.1

*Primary Examiner*—James R. Feyrer

*Attorney, Agent, or Firm*—Foley & Lardner

[57] ABSTRACT

An Anthurium plant named Passion having abundant magenta pink flowers which gradually fade to light pink. The flowers are held above the foliage. The plant flowers early, and attains a marketable size quickly. The leaves are medium green, glossy and durable. The plant habit is branched, upright and compact. It is tolerant to heat.

1 Drawing Sheet

The present invention comprises a new and distinct cultivar of Anthurium, botanically known as *Anthurium hybrid,* and referred to by the cultivar name Passion.

The new cultivar is a product of a breeding program carried out by the inventors Ann E. Lamb and Robert D. Hartman in Palmdale, Fla. The seedling is a result of a cross made by the inventors between unknown parents in Palmdale, Fla. The cultivar was discovered from the progeny of the stated cross by Ann E. Lamb. Tissue culture was used to increase the number of plants for evaluation and has demonstrated the stability of the combination of characteristics of Passion from generation to generation.

The following observations, measurements and values describe plants grown in Homestead, Fla. under shade-house conditions which closely approximate those generally used in horticultural practice.

The following traits have been repeatedly observed to be characteristics which in combination distinguish Passion from other Anthuriums of the same general type, for example, the cultivar Pink Aristocrat disclosed in U.S. Plant Pat. No. 7,441, to which comparative reference is made.

1. The plant produces abundant magenta pink flowers which gradually fade to pink.
2. The flowers are held above the foliage.
3. The leaves are medium green, with a glossy surface, and are durable.
4. The plant habit is compact, branched and upright.
5. The plant begins flowering early, attaining marketable size quickly.
6. The plant is heat tolerant.

All color references are measured against the Royal Horticultural Society Colour Chart. Colors are approximate as color depends on horticultural practices such as light level and fertilization rate, among others, without, however, any variance in genotype.

The color photographic drawing comprises a top perspective view of the inflorescence and foliage of a plant of Passion in a 15.3 cm pot approximately 28 weeks after planting a 20 week old liner obtained by tissue culture and grown under appropriate growing conditions. Colors are as accurate as possible with color illustrations of this type.

Origin: Seedling of unknown parentage.

Classification: *Anthurium hybrid,* cv, Passion.

Propagation: Asexual production either by tissue culture or division.

Plant: In a 15.3 cm pot for a plant grown from a 20 week old liner after 28 weeks under appropriate growing conditions, Passion reaches a mature size of approximately 20 cm. to 25 cm. in height and approximately 35 cm to 46 cm. in width.

*Leaves.*—Form: The leaf blade is ovate with a cuspidate tip and an obtuse to truncate base. The margins are entire. The midrib tends to curve somewhat downward over the length of the leaf. The leaf blade is flat. Size: Leaf blades of a mature sized plant are approximately 13 cm to 15 cm in length and approximately 6.6 cm to 7.3 cm in width. Petiole: The petiole is approximately 17.1 cm to 18.4 cm in height from the base of the petiole to the base of the leaf blade on the primary shoot. Secondary shoots are somewhat smaller depending on the age of the shoot. The petiole is approximately 2.5 mm in diameter just below the geniculum. The petiole below the geniculum is straight. Petiole Wings: Petiole wings are approximately 8.5 mm in length and approximately 3 mm in width at their midpoint. The tip of the petiole wing is rounded. There is approximately 14.3 cm to 16.5 cm between the top of the wing and the base of the geniculum. Geniculum: The geniculum is approximately 19 mm to 22 mm in length, approximately 3 mm in diameter, and is often curved. The color is 144A. There is no space between the top of the geniculum and the base of the leaf blade. Veins: Veins are sunken, with the leaf blade slightly convex between veins on the upper surface. The midrib protrudes from the upper surface of the leaf for approximately two-thirds the length of the leaf. Well-defined primary veins on leaves radiate out from the juncture of the petiole and the leaf. Veins stand out prominently on the lower side. There are approximately 4–6 primary veins on the leaf. Lobes: The leaf has two rounded lobes which do not extend past the petiole. The distance from the petiole/leaf juncture to the highest point on the lobes is approximately 2.7 cm to 3.0 cm. Colors: Upper surface: 137A. Lower surface: 146B. Midrib, upper surface: 144A. Midrib, lower surface: 146D. Petiole: Darker than, but closest to, 144A. Petiole wing: 145A.

Inflorescence:

Immature: The spathe is tightly rolled around the spadix and extrudes from the petiole sheath. The spathe is fully open approximately when the pedicel is fully elongated, about 22 cm to 27 cm above the soil surface.

*Mature.*—Spathe: Size: The flattened spathe is approximately 3.7 cm to 5.1 cm long and approximately 2.7 cm to 3.8 cm in width. Color: Fully open: Upper surface 66D; Lower surface 51D. Faded: Upper surface 49C–D; Lower surface 19 D with streaks of 146C. Arrangement: The spathe stands up on straight wiry pedicels and opens vertically above the leaves.

Shape: The spathe is ovate with a cordate base and a cuspidate tip. It is slightly cupped, with a wavy margin when first open, but flattens as it ages. Flowering time: After approximately 7 months from a 20 week old liner for an untreated plant as illustrated in sheet 1 and depending on season, approximately 6 to 8 blossoms will be present. Smaller blossoms may occur on less mature growth. First flowers are typically produced approximately 3–4 months after planting a 20 week old liner. Approximately 1 to 3 flowers are present.

Reproductive organs:

*Spadix.*—Size: Approximately 2.7 cm to 5.5 cm in height and approximately 5 mm to 6 mm in width. Color: When the spathe unrolls, the spadix is pinker than, but closest to 79D, gradully changing to 63D. Stamens: Anthers and filaments are not clearly visible. Pollen: White in color. Pistil: 78D in color, protruding between the staminate flowers, firmly fixed to the main axil. The pistilate flowers extend approximately 0.2 mm beyond the staminate flowers.

Roots: White fleshy roots with fine laterals.

It is claimed:

1. A new and distinct cultivar of Anthurium plant named Passion, as illustrated and described.

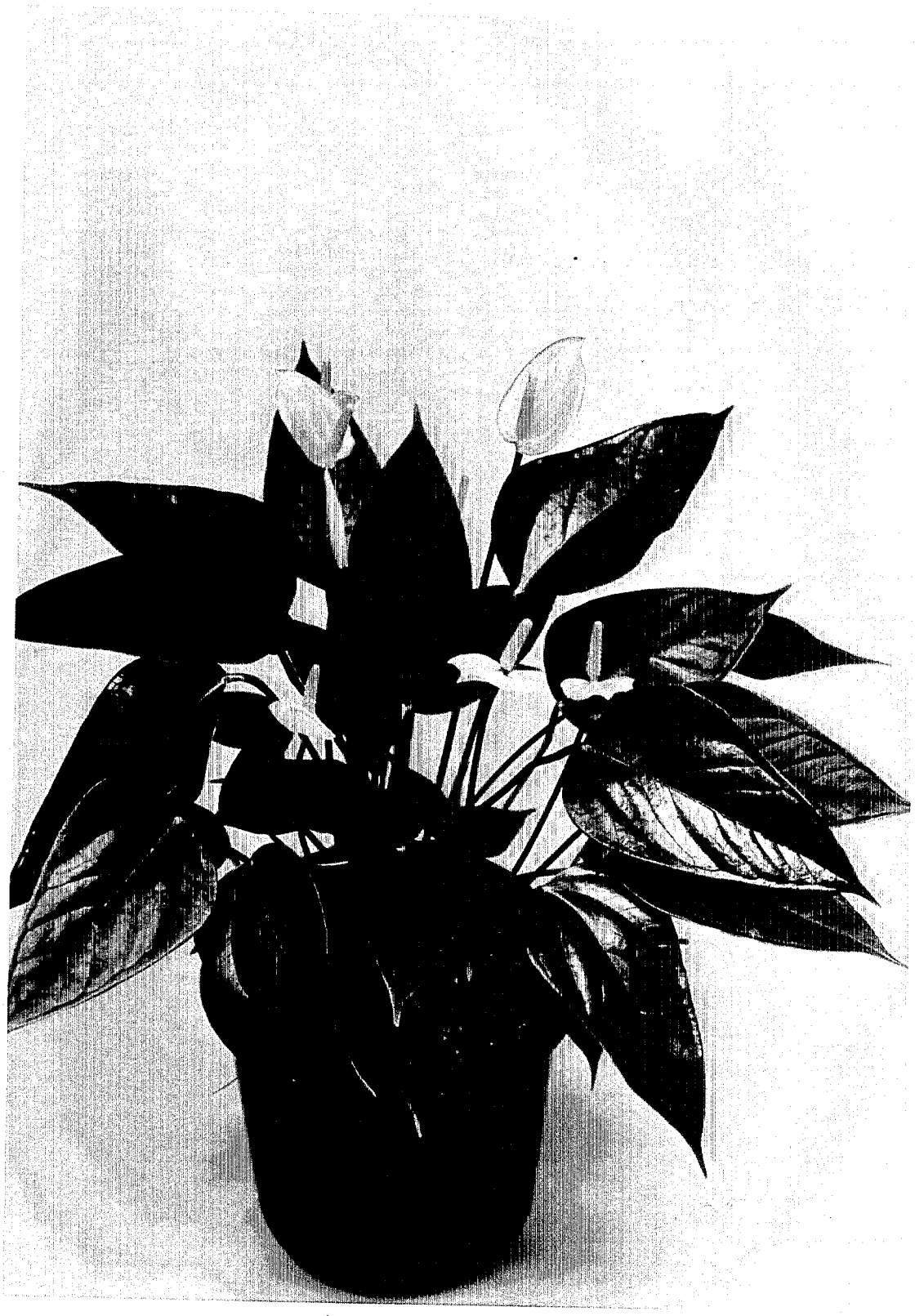

* * * * *